_United States Patent_ [19]

Earley

[11] 4,156,788

[45] May 29, 1979

[54] PROCESS FOR PURIFICATION OF TETRAMETHYLBIPHENOL BY ENTRAINMENT SUBLIMATION

[75] Inventor: Roger A. Earley, Wilmington, Del.

[73] Assignee: ICI Americas Inc., Wilmington, Del.

[21] Appl. No.: 834,123

[22] Filed: Sep. 19, 1977

[51] Int. Cl.$^2$ ............................................. C07C 37/22
[52] U.S. Cl. .................................................... 568/730
[58] Field of Search .......................... 260/620; 568/730

[56] References Cited

U.S. PATENT DOCUMENTS

| | | | |
|---|---|---|---|
| 3,812,193 | 5/1974 | Randell et al. ....................... | 260/620 |
| 4,067,890 | 1/1978 | Rutledge .............................. | 260/620 |
| 4,070,383 | 1/1978 | Rutledge .............................. | 260/620 |

OTHER PUBLICATIONS

Perry et al., "Chem. Eng. Handbook", 4th Edition, pp. 17-23-17-26, (1963).

_Primary Examiner_—Norman Morgenstern
_Attorney, Agent, or Firm_—H. Jolyon Lammers

[57] ABSTRACT

Substantially pure tetramethylbiphenol may be recovered from a reaction product obtained by the oxidative coupling of xylenol by vaporizing the reaction product and subliming substantially pure tetramethylbiphenol from the vapor.

10 Claims, No Drawings

PROCESS FOR PURIFICATION OF TETRAMETHYLBIPHENOL BY ENTRAINMENT SUBLIMATION

FIELD OF THE INVENTION

The present invention concerns a process for purifying crude tetramethylbiphenol by entrainment or vacuum assisted sublimation. More specifically, the invention concerns a process of separating substantially pure tetramethylbiphenol from a mixture containing tetramethylbiphenol and one or more of xylenol, cresol, tetramethyldiphenoquinone, high molecular weight polyarylene ethers, low molecular weight oligomers and inorganic impurities by entrainment or vacuum assisted sublimation.

DESCRIPTION OF THE PRIOR ART

Tetramethylbiphenol is commonly prepared by oxidative coupling of 2,6-xylenol. Depending on which oxidative coupling process is used to prepare the crude TMBP, the conversion to TMBP may range from 14% from a continuous process up to 75% or higher from a batch process. Present techniques for separating the tetramethylbiphenol (TMBP) from the oxidative coupling reaction mixture involve filtration and crystallization. Neither of these techniques, however, are very effective for economically separating tetramethylbiphenol from all of the reaction by-products. The degree of purity normally obtained by the aforesaid methods rarely exceeds 98 percent unless the prior art separation techniques are repeated with partially purified tetramethylbiphenol.

Prior art separation techniques suggest the removal of the polyarylene ether and xylenol by washing the reaction mixture with a solvent in which these materials are soluble, such as for example toluene, benzene, or a halogenated solvent such as methylene chloride. A second distillation step is suggested to separate the dissolved components from each other and the solvent. If the reaction mixture contains TMBP and tetramethyldiphenoquinone, these materials may be separated by stirring the solid product with a dilute aqueous solution of sodium hydroxide, which converts the TMBP to the water soluble sodium salt. The insoluble tetramethyldiphenoquinone may then be filtered off and the TMBP recovered by adding the aqueous solution of the sodium salt thereof to a dilute solution of an acid such as hydrochloric acid from which the TMBP may be precipitated.

A frequency complaint has been the difficulty in removing the dimer which has the same molecular weight and similar chemical structure as TMBP. A further drawback of such known separation techniques is that they require the use of expensive organic solvents which may cause injury to health and environment in the absence of costly antipollution devices.

SUMMARY OF THE INVENTION

It is a primary object of the present invention to eliminate the above described drawbacks of the prior art by providing an economic sublimation technique for obtaining substantially pure tetramethylbiphenol in high yields from crude tetramethylbiphenol. Accordingly, there is provided a process for recovering substantially pure tetramethylbiphenol from a mixture containing tetramethylbiphenol, and one or more of xylenol, cresol, tetramethyldiphenoquinone, high molecular weight polyarylene ethers and low molecular oligomers, which comprises heating the mixture in a still to a temperature of from about 200° to 350° C. at atmospheric pressure to vaporize the tetramethylbiphenol, transporting the vapor from the still to a collection zone, collecting the sublimed tetramethylbiphenol in the collection zone at a temperature of from 150° to 220° C. and recovering the substantially pure tetramethylbiphenol from the collection zone.

DESCRIPTION OF THE INVENTION

In producing tetramethylbipenol by the oxidative coupling of xylenol the crude reaction product may contain in additon to tetramethylbiphenol unreacted xylenol, cresol low molecular weight oligomers, tetramethyldiphenoquinone, high molecular weight polyarylene ether and, depending on the specific oxidative coupling process, used residual catalyst. The components of such a reaction mixture may be represented by the following formulas:

Tetramethylbiphenol

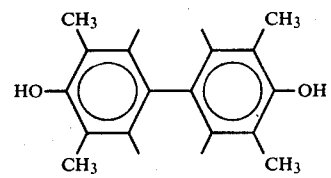

Tetramethyldiphenoquinone

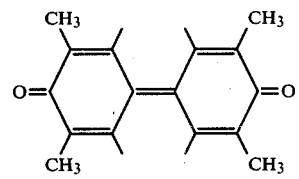

Low molecular weight oligomers, such as for example, the dimer

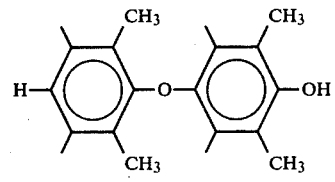

High molecular weight polyarylene ether

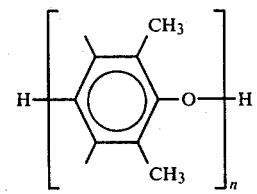

Unreacted xylenol, such as for example, 2,6-xylenol

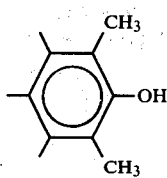

Cresol, such as for example meta-cresol

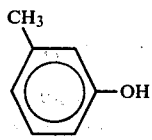

Catalytic residue of commonly used oxidative coupling reaction may include oxides such as for example oxides of copper, cobalt, iron, nickel, manganese, palladium and molybdenum. Similarly, metals have also been used to form effective catalytic chelates with such materials as imino acids, amines, ammonia, glycinates and oximes. See for example U.S. Ser. Nos. 634,644, 655,104, and 666,228.

It has now been discovered that by heating such a crude reaction product in a still to about 200° to 350° C. the tetramethylbiphenol after being vaporized will sublime free of dimer at a temperature of from about 150° to 220° C. Additionally, its been noted that a carrier gas or an entrainer, as opposed to natural convection, greatly increases the mass transfer and provides a commercially attractive recovery rate by efficiently transporting the sublimable vapor from a still vessel to a collection vessel.

While it is not absolutely essential that the entrainer be hot as it enters the still, it is desirable since external heat transfer to the entrainer is less difficult than heating the entrainer in the still. A heated entrainer also tends to avoid premature sublimation in the still. The economically optimum temperature of the entrainer entering the still is slightly above the temperature at which the still is operated.

The specific sublimation equipment utilized during the method of invention does not appear critical. Similarly, the method of heating and cooling the varous vaporization and collection zones has also been deemed to be unimportant. A variety of equipment and temperature controlling methods are known to the one skilled in the art and may be utilized. See for example, Journal of Chemical Engineering, September 1951, pages 157–166.

Process Conditions

In general the crude reaction mixture is heated in the still to a temperature of at least 200° C. to insure complete vaporization of the tetramethylbiphenol present. Temperatures as high as 350° C. may however occur without effecting the recovery technique. A preferred still temperature however, dictated partially by economic consideration, is at about 275° C. At temperatures higher than 350° C. some of the reaction components may break down, causing the introduction of unknown variables during the sublimation process. Temperatures below about 275° C. detrimentally affect the rate of vaporization of TMBP.

The vapor containing TMBP and xylenol passes to a first collection zone or vessel. The first collection zone or vessel should have a temperature of about 150° to 220° C. The melting point of tetramethylbiphenol is about 223° C. and a preferred range would therefore occur from 160° to 180° C. It has been discovered that temperatures in the cooling zone of about 170° C. provide for the highest purity of tetramethylbiphenol.

To avoid formation of undesirable by products such an additional low molecular oligomers it is suggested to subject the crude cake to an acid wash prior to placing the cake into the still.

The xylenol vapor may be passed through the first collection zone downstream to a second collection zone where it may be recovered for recycle. The nonvolatized components remain in the still from which they may be drained.

Too low a temperature for the crude reaction product obviously decreases the yield and the rate of recovery of product and too high a temperature produces economic inefficiencies in that energy is wasted both in heating the vapor and in cooling it. Short heating times are advantageous but require a large area for volatilization. With smaller areas, longer heating times, are necessary to permit adequate recovery of products. It is important that the presence of oxygen or air is excluded during the vaporization and sublimation phases since there is a tendency for tetramethylbiphenol when exposed to even small amounts of air to be oxidized to tetramethyldiphenoquinone.

The sublimation process of the invention also includes the use of a vacuum to increase the flow of vaporization from the still into the collection zones. The term entrainment sublimation is meant to include such sublimation processes assisted by vacuum. Naturally the process temperatures of vacuum assisted sublimation techniques will vary somewhat depending on the difference between the existing ambient pressures and atmospheric pressures.

As mentioned hereinbefore, the reaction mixture may contain metallic catalytic residues. Should such residues be valuable, the catalyst may be leached out prior to or after the vaporization of tetramethylbiphenol.

The tetramethylbiphenol produced in accordance with the method of the invention is suitable for any use heretofore described in the art. Thus, the biphenol may be employed as stabilizer in gasoline and other petroleum products such as described in U.S. Pat. No. 2,479,948 issued to Luten et al. or the biphenols may be considered as intermediate reaction products which may be further reacted to form polycarbonates, epoxies or polysulfones.

In order to describe the present inventions so it may be more clearly understood the following examples are set forth. These examples are given primarily for the purpose of illustration and any enumeration of detail contained therein should not be interpreted as a limitation on the concept of the present invention.

EXAMPLE 1

Into a reaction chamber there was added a reaction product obtained from a oxidative coupling process of xylenol which consisted of 15.1 percent by weight of water 72.7 percent by weight of tetramethylbiphenol 0.2 percent by weight of tetramethyldiphenoquinone, less than 0.001 percent by weight of copper, and 4.1 percent by weight of a mixture of high molecular weight polyarylene ether and low molecular weight oligomer and 7.9 percent 2,6-xylenol. The reaction mixture was heated to a temperature of 260° C. and the vapors eminating from the reaction mixture were allowed to pass to a wall cooled collection zone which was maintained at a temperature of 183° C. degrees. A second collection zone connected to the first collection zone was provided with a cooling temperature of 17° C. After a period of time to bring the still to temperature a white crystalline product was removed from the first collection zone which upon analysis showed to be 99.9+ percent of tetramethylbiphenol having a melting point between 223° and 225° C. Based on the amount of TMBP removed from the still the first collection zone had an efficiency 99.7 percent in recovering TMBP.

EXAMPLE 2

Into a reaction chamber there was added a reaction product obtained from a oxidative coupling process or xylenol which consisted of 0.2 percent by weight of water 98.7 percent by weight of tetramethylbiphenol 0.0069 percent by weight of tetramethyldiphenoquinone, 0.0002 percent by weight of copper, and 1.1 percent by weight of a mixture of high molecular weight polyarylene ether and low molecular weight oligomer and a trace of 2,6-xylenol. The reaction mixture was heated to a temperature of 250° C. and the vapors eminating from the reaction mixture were allowed to pass to a wall cooled collection zone which was maintained at a temperature of 185° C. A second collecton zone connected to the first collection zone was provided with a cooling temperature of 23° C. After a period of time to bring the still to temperature a white crystalline product was removed from the first collection zone which upon analysis showed to be 99.9 percent of tetramethylbiphenol having a melting point between 222° to 224° C.

EXAMPLE 3

Into a reaction chamber there was added a reaction product obtained from a oxidative coupling process or xylenol which consisted of 0.2 percent by weight of water 98.6 percent by weight of tetramethylbiphenol 0.2 percent by weight of tetramethyldiphenoquinone, 0.0013 percent by weight of copper, 0.07 percent by weight of sodium, and 0.2 percent by weight of a mixture of high molecular weight polyarylene ether and low molecular weight oligomer and 1.2 percent 2,6-xylenol. The reaction mixture was heated to a temperature of 280° C. and the vapors eminating from the reaction mixture were allowed to pass to a collection zone which was maintained at a temperature of 160° C. by a counter current of inert cooling gas. A second collection zone connected to the first collection zone was provided with a cooling temperature of 6° C. After a period of time to get to still temperature a white crystalline product was removed from the first collection zone which upon analysis showed to be 99.8 percent of tetramethylbiphenol having a melting point of about 223° C. Based on the amount of TMBP removed from the still the first collection zone had an efficiency approximately 99.0 percent in recovering TMBP.

EXAMPLE 4

Into a reaction chamber there was added a reaction product obtained from a oxidative coupling process or xylenol which consisted of 0.1 percent by weight of water 98.3 percent by weight of tetramethylbiphenol 0.2 percent by weight of tetramethyldiphenoquinone, 0.0002 percent by weight of copper, and 1.0 percent by weight of a mixture of high molecular weight polyarylene ether and low molecular weight oligomer and 0.7 percent 2,6-xylenol weight. The reaction mixture was heated to a temperature of 310° C. and the vapors eminating from the reaction mixture were allowed to pass to collection zone which was maintained at a temperature of 150° by a counter current of inert cooled gas. A second collection zone connected to the first collection zone was provided with a cooling temperature of about room temperature. After a period of time to get the still to temperature a white crystaline product was removed from the first collection zone which upon analysis showed to be 99.8 percent of tetramethylbiphenol having a melting point of about 223° C.

EXAMPLE 5

Into a reaction chamber there was added a reaction product obtained from a oxidative coupling process or xylenol which consisted of 0.2 percent by weight of water 98.6 percent by weight of tetramethylbiphenol 0.2 percent by weight of tetramethyldiphenoquinone, 0.0013 percent by weight of copper, and 0.2 percent by weight of a mixture of high molecular weight polyarylene ether and low molecular weight oligomer and 1.2 percent by weight of 2,6-xylenol. The reaction mixture was heated to a temperature of 340° C. and the vapors eminating from the reaction mixture were allowed to pass to collection zone which was maintained at a temperature of 195° C. by counter current of inert cooled gas. A second collection zone connected to the first collection zone was provided with a cooling temperature of 6° C. After a period of time to bring the still to temperature a white crystalline product was removed from the first collection zone which upon analysis showed to be 99.2 percent of tetramethylbiphenol having a melting point between about 222° and 223° C.

What is claimed is:

1. A process for recovering substantially pure tetramethylbiphenol from a mixture containing tetramethylbiphenol, and one or more of xylenol, cresol, tetramethyldiphenoquinone, high molecular weight polyarylene ethers, low molecular oligomers and inorganic impurities which comprises heating the mixture in a still to a temperature of from about 200° to 350° C. to vaporize the tetramethylbiphenol, transporting the vapor from the still to a collection zone, subliming the tetramethylbiphenol in the collection zone at a temperature of from 150° to 220° C. and recovering the substantially pure tetramethylbiphenol from the collection zone.

2. A process as claimed in claim 1 wherein the introduction of vapor into the collection zone is promoted by a flow of a heated inert gas.

3. A process as claimed in claim 2 wherein the gas is nitrogen.

4. A process as claimed in claim 2 wherein the gas is hydrogen.

5. A process as claimed in claim 1 wherein the introduction of vapor into the collection zone is promoted by a vacuum.

6. A process as claimed in claim 1 wherein the tetramethylbiphenol in the collection zone is sublimed at a temperature of from 160° to 180° C.

7. A process as claimed in claim 1 wherein the collection zone temperature is maintained by a counter current of cooled inert gas.

8. A process as claimed in claim 1 wherein the vapor is passed from the collection zone to a second collection zone where xylenol may be recovered at temperatures of less than 25° C.

9. A process as claimed in claim 1 wherein the mixture is subjected to a leaching operation to remove catalytic residue prior to heating.

10. A process as claimed in claim 1 wherein the mixture is subjected to an acid wash prior to heating.

* * * * *

UNITED STATES PATENT AND TRADEMARK OFFICE
CERTIFICATE OF CORRECTION

PATENT NO. : 4,156,788
DATED : May 29, 1979
INVENTOR(S) : ROGER A. EARLEY

It is certified that error appears in the above-identified patent and that said Letters Patent are hereby corrected as shown below:

Column 1, line 51 change "A frequency" to --A frequent--.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks